United States Patent [19]

Helfer

[11] 4,301,806

[45] Nov. 24, 1981

[54] ROTATING MECHANISM FOR INTRODUCING A FETAL ELECTRODE

[75] Inventor: Joel N. Helfer, New Haven, Conn.

[73] Assignee: American Home Products Corporation, New York, N.Y.

[21] Appl. No.: 140,366

[22] Filed: Apr. 14, 1980

[51] Int. Cl.³ .............................................. A61B 5/04
[52] U.S. Cl. ................................................. 128/642
[58] Field of Search ...................... 128/642, 639, 785

[56] References Cited

U.S. PATENT DOCUMENTS

| Re. 28,990 | 10/1976 | Hon et al. | 128/642 |
|---|---|---|---|
| 3,750,650 | 8/1973 | Ruttgers | 128/642 |
| 3,910,271 | 10/1975 | Neward | 128/642 |
| 3,986,497 | 10/1976 | Dali | 128/642 |
| 4,149,528 | 4/1979 | Murphy | 128/642 |

FOREIGN PATENT DOCUMENTS 4785 10/1979 European Pat. Off. ............ 128/642

*Primary Examiner*—Lee S. Cohen
*Attorney, Agent, or Firm*—Eugene L. Flanagan, III

[57] ABSTRACT

An improved electrode structure for use in monitoring fetal heartbeat and the like. A guide tube has an open forward end adapted to be inserted through the vagina and cervix of a woman in labor. A signal acquisition device, adapted to rotatably engage a fetal epidermis, is slidably and rotatably disposed in the guide tube. A driving member is slidably and rotatably disposed in the guide tube for driving the signal acquisition device into engagement with a fetal epidermis. A line is attached to the driving member and is wrapped circumferentially around at least a portion of the driving member. A device is affixed to the line for pulling it tangentially with respect to the drive member, whereby the driving member and the signal acquisition device may be rotated for engaging a fetal epidermis.

9 Claims, 8 Drawing Figures

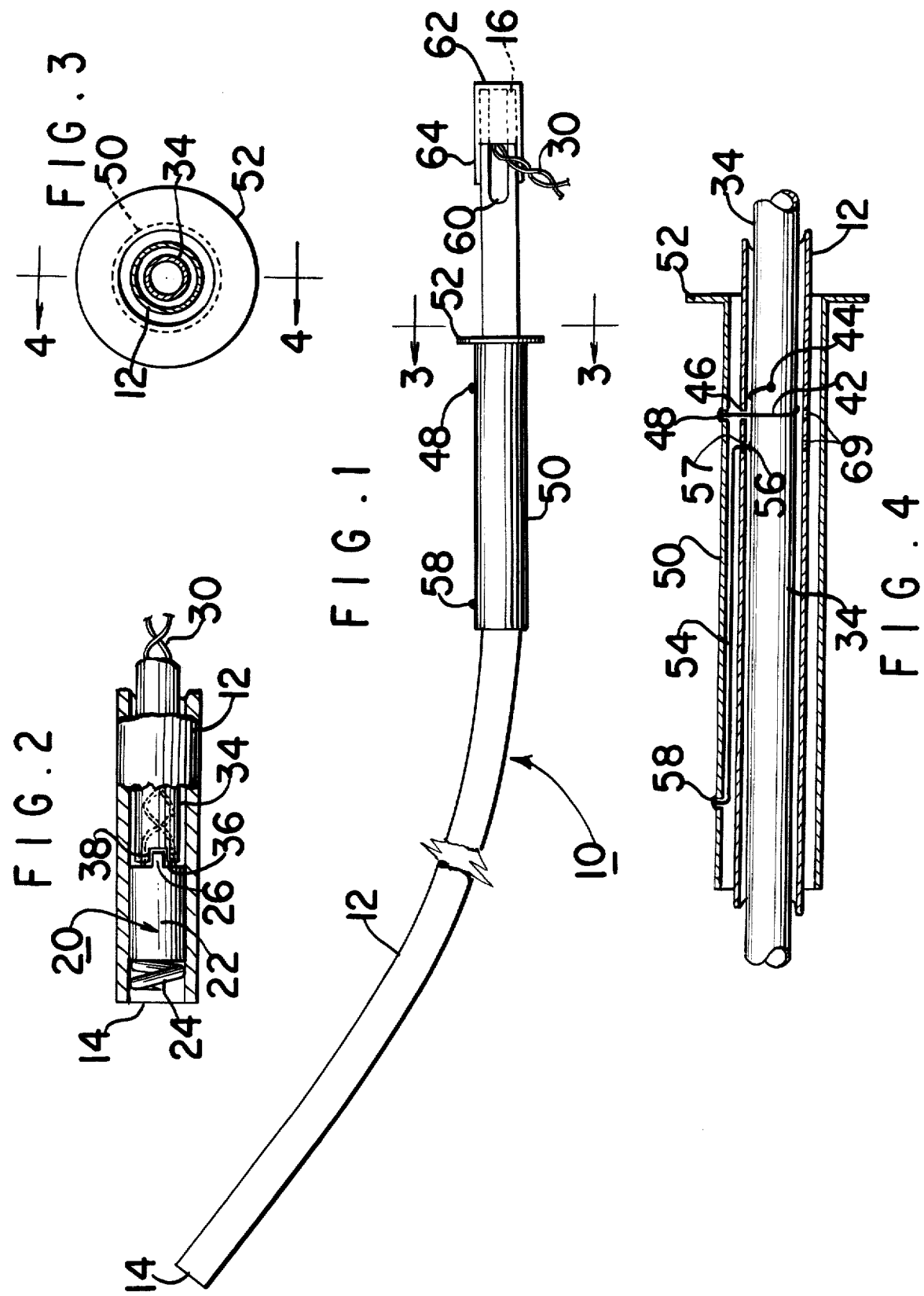

ROTATING MECHANISM FOR INTRODUCING A FETAL ELECTRODE

BACKGROUND OF THE INVENTION

The present invention relates to electrode structures for use in acquiring a biosignal from a fetus. More particularly, the present invention relates to such electrodes which are introduced into body tissue by a rotary motion.

U.S. Pat. No. Re. 28,990 to Edward H. Hon and Robert W. Hon discloses an electrode system for monitoring fetal heartbeat wherein a retaining coil mounted on a holder member is rotatably introduced into a fetal epidermis by a flexible drive tube rotated by hand. The retaining coil on its holder together with the drive tube are slidably and rotatably disposed in a guide tube which is inserted through the woman's vagina and cervix.

In order to render such a device easier to use, it is desirable to eliminate the need for the drive tube to be rotated manually. In U.S. Pat. application Ser. No. 21,550 filed Mar. 20, 1979 in the name of Edward D. Hon, a plunger is mounted within the guide tube and, when moved toward the forward end of the guide tube by a force supplied thereto by the physician, causes a helical thread-type means to rotate the holder and the spiral retaining coil into a fetal epidermis. However, helical drive mechanisms are relatively complex and expensive to manufacture.

SUMMARY OF THE INVENTION

In accordance with one aspect of the present invention, an improved electrode structure is provided for use in monitoring fetal heartbeat and the like. A guide tube having an open forward end is adapted to be inserted through the vagina and cervix of a woman in labor. A signal acquisition means which is adapted to rotatably engage a fetal epidermis, is slidably and rotatably disposed in the guide tube. A driving member which is also slidably and rotatably disposed in the guide tube is provided for driving the signal acquisition means into engagement with a fetal epidermis. A first line is attached at a first end to the driving member and is circumferentially wrapped around at least a portion of the driving member. A line unwinding means is affixed to a second end of the line for pulling the line tangentially with respect to the driving member, whereby the driving member and the signal acquisition means may be rotated for engaging a fetal epidermis. Accordingly, the present invention dispenses with the need for a helical drive mechanism and is readily implemented with electrode systems of the type disclosed in U.S. Pat. No. Re. 28,990.

In accordance with a further aspect of the present invention, the line unwinding means comprises means for withdrawing the first line through an aperture in the guide tube such that the drive tube is thereby caused to rotate relative to the guide tube upon actuation of the line unwinding means. Preferably, the means for withdrawing the first line comprises a slide mounted externally to the guide tube and movable axially with respect thereto for withdrawing the first line through the aperture.

In accordance with yet another aspect of the present invention, the electrode structure comprises retaining means for retaining the signal acquisition means within the guide tube while the first line remains fully wrapped on the driving member. In embodiments wherein the first line is withdrawn through a first aperture in the guide tube to cause the drive member to rotate relative to the guide tube, the retaining means comprises displacement means for displacing the first end of the first line rearwardly of the first aperture. Preferably, the displacement means comprises a second line attached at a first end to the drive member at a point spaced axially at a first distance from the first end of the first line. The second line passes through a second aperture in the guide tube and is affixed at a second end to the line unwinding means, such that when the first line is fully wound on the drive member, the first end of the second line is then axially aligned with the second aperture. The first aperture is spaced axially from the second aperture by a second distance which is sufficiently smaller than the first distance so that when the first line is fully wound on the drive member, the latter is withdrawn sufficiently into the guide tube to permit retention of the signal acquisition means therein. Means are provided for maintaining the signal acquisition means against the forward end of the drive member. Therefore, unintentional engagement of the retaining coil with the mother's vagina or cervix is avoided.

Where the line unwinding means comprises a slide mounted externally to the guide tube for axial movement with respect thereto, the second end of the second line preferably is affixed to the slide at a distance spaced axially from the second end of the first line, such that when the first line is unwound by an axial motion of the slide, the second line is caused to wind about the drive member. With this motion, tension is placed on the first line, such that the drive tube is moved forwardly, carrying the signal acquisition means through the open forward end of the guide tube for engagement with a fetal presenting part. As the second line is thus wound about the drive member, an opposed axial motion of the slide will unwind the second line, causing the drive member to rotate in the opposite direction and the first line to rewind about the drive member to permit a reapplication of the signal acquisition means in the event the first try was unsuccessful.

DESCRIPTION OF THE DRAWINGS

FIG. 1 is an elevational view of an improved electrode structure for use in monitoring fetal heartbeat and the like.

FIG. 2 is a partially sectional view of the forward end of the electrode structure of FIG. 1.

FIG. 3 is a sectional view of the electrode structure of FIG. 1, taken along lines 3—3 of FIG. 1.

FIG. 4 is a partially sectional view of the electrode structure of FIG. 1, taken along the lines 4—4 of FIG. 3.

DESCRIPTION OF PREFERRED EMBODIMENTS

Figure 5:
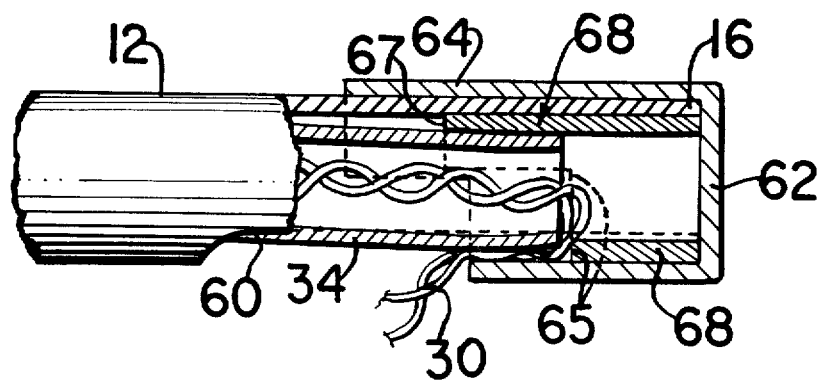
FIG. 5 is a partially sectional view of the rear end of the electrode structure of FIG. 1.

With reference to FIG. 1, an electrode structure 10 in accordance with the present invention comprises a guide tube 12 having an open forward end 14 and an open rear end 16. The guide tube 12 is curved and form-sustaining to facilitate insertion of the tube through the vagina and cervix of a woman in labor. It is made preferably of nylon.

With reference to FIG. 2, a signal acquisition means 20 comprises a cylindrical holder member 22, a spiral retaining coil 24 mounted at the forward end of cylindrical holder member 22 and a fin 26 mounted at the rear end of cylindrical holder member 22. Signal acquisition means 20 is slidably and rotatably disposed in the forward end of the guide tube 12. Spiral retaining coil 24 is made of stainless steel and has a sharpened forward end such that when signal acquisition means 20 is slid forwardly past forward end 14 when the latter is pressed against a fetal presenting part, the signal acquisition means 24 may be rotated such that coil 24 engages the fetal epidermis to sense a voltage representative of the physical condition of the child, such as fetal heartbeat and other conditions. Fin 26 is likewise made of stainless steel and serves as a reference electrode. One each of a pair of electrode wires 30 is conductively affixed to coil 24 and fin 26 to conduct the signal developed thereacross to a monitoring apparatus. Further information regarding signal acquisition means 20 is disclosed in U.S. Pat. No. Re. 28,990 in FIGS. 8, 9 and 10 thereof and in the corresponding portions of the specification. The disclosure of U.S. Pat. No. Re. 28,990 is incorporated herein by reference.

A driving member 34 comprising a flexible tube slidably and rotatably disposed in the guide tube 12 is provided for driving the signal acquisition means 20 into engagement with a fetal epidermis. The driving member 34 has a forward end 36 recessed from the forward end 14 of the guide tube. A notch 38 is provided in forward end 36 to engage fin 26 of the signal acquisition means 20 in order to impart rotational motion thereto. Driving member 34 also serves to advance the signal acquisition means 20 through the forward end 14 of the guide tube 12 to engage a fetal epidermis. The driving member 34 extends rearwardly through the guide tube 12 to an open rear end thereof adjacent rear end 16 of guide tube 12 and recessed slightly within the guide tube. Driving member 34 is made preferably of low or medium density polyethylene, which renders it sufficiently flexible to rotate in the curved guide tube. The use of this material also limits the torque applied to the fin 26 by permitting it to slip from notch 38 when excessive torque is applied.

Means are provided for advancing the signal acquisition means forwardly through end 14 of guide tube 12 and for rotating the signal acquisition means to engage a fetal epidermis. With reference to FIGS. 1, 3 and 4, first line 42, preferably made of monofilament, is attached at a first end 44 to driving member 34 and, prior to application of the signal acquisition means to a fetus, is wound counter-clockwise when viewed from the rear of driving member 34, and circumferentially around the driving member by approximately 450° (approximately 1¼ wraps around the driving member). First line 42 may be affixed to driving member 34 by forming an aperture therein, expanding the outer diameter of the first end 44 of line 42 by the application of heat and passing the line 42 through the aperture in driving member 34 until the first end 44 abuts the inner wall of driving member 34 forming the aperture. The line 42 extends tangentially from the outer surface of the driving member 34 through a first aperture 46 in the guide tube 12. A second end 48 of the first line 44 extends through an aperture in a sliding means in the form of a cyclindrical sleeve 50 mounted externally to guide tube 12 about a portion thereof adjacent its rear end 16 which is substantially straight, such that sleeve 50 may be slid axially along the guide tube. Sleeve 50 may be made of polyethylene or any suitable plastic. The second end 48 of the first line 42 is prevented from slipping through the aperture in the sleeve 50 by expanding the outer diameter of the line through the application of heat, as in the case of first end 44. The portion of sleeve 50 closest to end 16 of guide tube 12 is expanded in the form of a radial flange 52 adapted to be grasped by the physician to apply a force thereto causing the sleeve 50 to slide axially with respect to the guide tube 12. This axial motion of the sleeve 50 serves to withdraw the first line 42 through the first aperture 46 such that the first line 42 is pulled tangentially with respect to the driving member 34 causing it to rotate relative to the guide tube 12. This, in turn, transmits a clockwise torque to the signal acquisition means 20 through the fin 26 thus to rotate the signal acquisition means 20.

A second line 54, also preferably made of monofilament, is attached at a first end 56 to driving member 34 in the same manner as first end 44 of first line 42, at a point displaced 90 degrees counterclockwise (when viewed from the rear) from the first end 44 of first line 42 and spaced axially therefrom by a first distance. Line 54 passes through a second aperture 57 in guide tube 12 and is affixed at a second end 58 to cylindrical sleeve 50 by passing it through an aperture therein in the same manner as second end 48 of first line 42 is affixed to sleeve 50. The second end 58 is positioned in radial alignment on sleeve 50 with second end 48 of first line 42 and is spaced axially therefrom by a distance such that when second end 48 is aligned axially with the aperture 56 in guide tube 12 and first line 42 is fully wound on driving member 34, first end 56 of second line 54 is in axial alignment with its respective aperture 57 in guide tube 12 and second line 54 is fully extended from the driving member 34. In addition, the apertures 46 and 57 in guide tube 12 are spaced apart by a second distance which is shorter than the first distance between first ends 44 and 56 of lines 42 and 54, respectively. Accordingly, in this position of the slide 50, the driving member 34 is fully withdrawn toward end 16 of guide tube 12. The axial length of driving member 34 is selected such that, when it is in the position described above, its forward end 36 is withdrawn sufficienty from forward end 14 of the guide tube 12 to permit complete withdrawal of the signal acquisition means 20 within guide tube 12.

It will be appreciated from the foregoing that, when sleeve 50 is pulled towards the rear 16 of guide tube 12, first line 42 will be withdrawn through aperture 46 in guide tube 12 thus to rotate the driving member 34 with respect thereto and to wind second ine 54 clockwise around driving member 34. This motion likewise causes driving member 34 to move towards the forward end 14 of guide tube 12 thus to extend the spiral retaining coil 24 therethrough to engage a fetal epidermis. It will be appreciated further that, when second line 54 has been wound clockwise on driving member 34, an opposed axial motion of the sleeve 50 will cause the driving member 34 to rotate counterclockwise thus to rewind first line 42 on driving member 34. Accordingly, should the spiral retaining coil 24 fail to make a proper connection to the fetal skin upon the first attempted application, the electrode structure 10 may be reset for a subsequent attempt.

With reference to FIGS. 1 and 5, a slot 60 is formed in the rear end 16 of guide tube 12 such that it extends approximately 90° radially and about 2.5 centimeters axially from end 16. Slot 60 preferably is aligned radially with the inner curvature of guide tube 12 for free movement of wires 30 through the driving member 34 at the time of application. It also permits the doctor to observe whether the signal acquisition means 20 is secured to the fetal presenting part. A cap 62 is fitted over the open rear end 16 and is provided with an axial extension 64 which acts as a stop preventing sleeve 50 from being pulled toward the rear of guide tube 12 beyond the length of first line 42. Cap 62 may be made of plastic. Electrode wires 30 extend from slot 60 in guide tube 12. A hollow plug 68 is fitted snugly in end 16 of guide tube 12. Plug 68 has a forwardly extending tab 67, such that the rear end of driving member 34 is retained frictionally against an inner surface thereof and a forward edge 65 of plug 68 serves to press electrode wires 30 against the rear of driving member 34 to prevent the signal acquisition means 20 from advancing through forward end 14 of guide tube 12 prior to use. Accordingly, plug 68 provides a means for maintaining the signal acquisition means 20 against the forward end 36 of driving member 34.

In accordance with a method of assembling the electrode structure 10, first and second lines 42 and 54 are each passed successively through one of two further apertures 69 in guide tube 12, each in axial alignment and diametrically opposed to a respective one of apertures 46 and 57. Two pairs of apertures are provided in driving member 34 such that one pair is aligned axially with the desired position of end 56 of line 54 and the other is aligned axially with the desired position of end 44 of line 42. Each aperture is diametrically opposed to the other of the pair and the pairs are displaced radially 90 degrees one from the other. Accordingly, after line 42 is passed through its respective aperture 69 in guide tube 12, it is passed through its respective pair of apertures in driving member 34, and then outwardly through aperture 46 in guide tube 12. The first end 44 of line 42 is held in one of the apertures of driving member 34 as described hereinbelow. When driving member 34 is rotated one and one quarter turns counterclockwise when viewed from the rear to wind first line 42 thereabout. Then driving member 34 is shifted axially and line 54 is passed through its respective aperture 69, its respective pair of apertures in driving member 34 and outwardly through aperture 57 in guide tube 12.

One each of the apertures in the pairs of apertures provided in driving member 34 has a larger diameter than that of the other aperture in the pair. First ends 44 and 56 of lines 42 and 54 are diametrically enlarged by heating such that they will pass through apertures 69 and the larger apertures in driving member 34, but be prevented from passing through the smaller apertures therein. Lines 42 and 54 are passed through their respective apertures in sleeve 50 and the latter is slid onto guide tube 12. Then lines 42 and 54 are cut and ends 48 and 58 thereof are formed in the same manner as ends 44 and 56. Electrode wires 30 are passed through the open forward end 36 of driving member 34 and are pulled through the rear thereof and slot 60 of guide tube 12, such that fin 26 of signal acquisition means 20 is seated in notch 38 of driving member 34. Plug 68 is inserted in the end 16 of guide tube 12 and the rear of driving member 34 is pressed thereinto such that wires 30 are wedged frictionally between member 34 and the bevelled surface 67 of plug 68. Then cap 62 is fitted over rear end 16 to complete the assembly of electrode structure 10.

Figure 6:
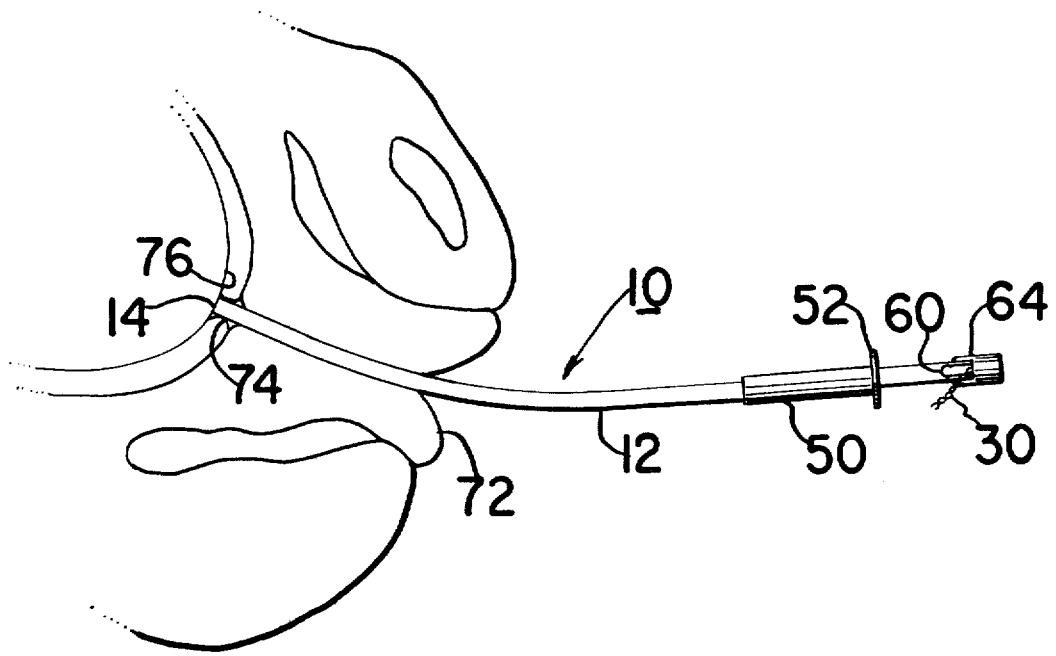
FIGS. 6, 7 and 8 are diagrammatic views illustrating the manner in which the electrode structure of FIGS. 1-5 is applied to a child in utero.
Figure 7:
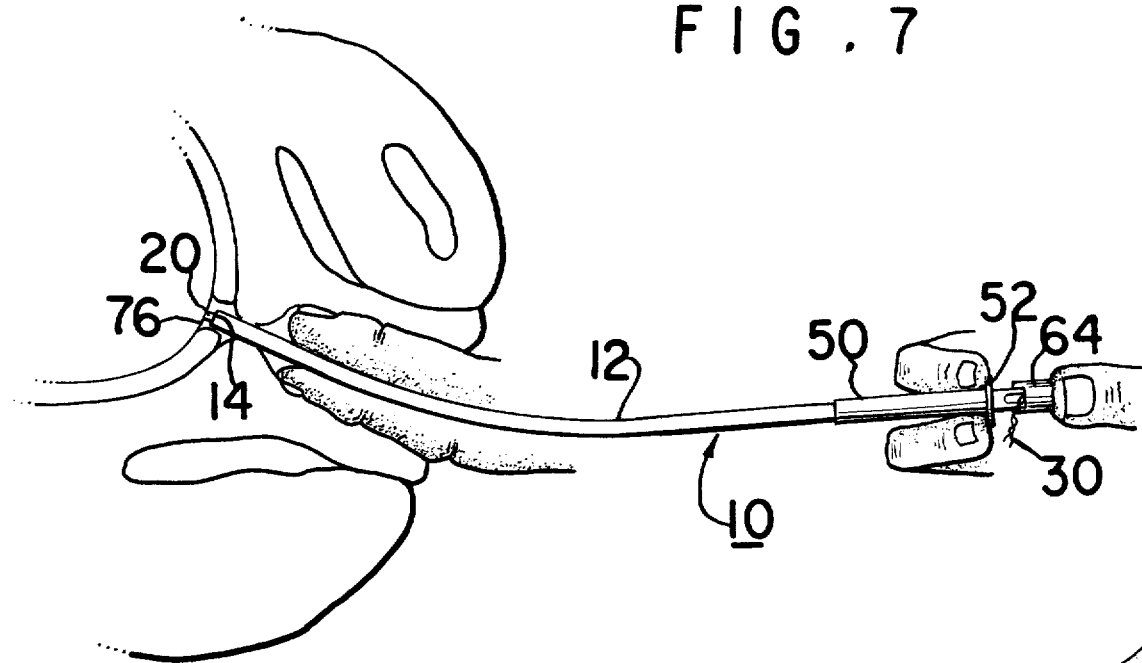
Figure 8:
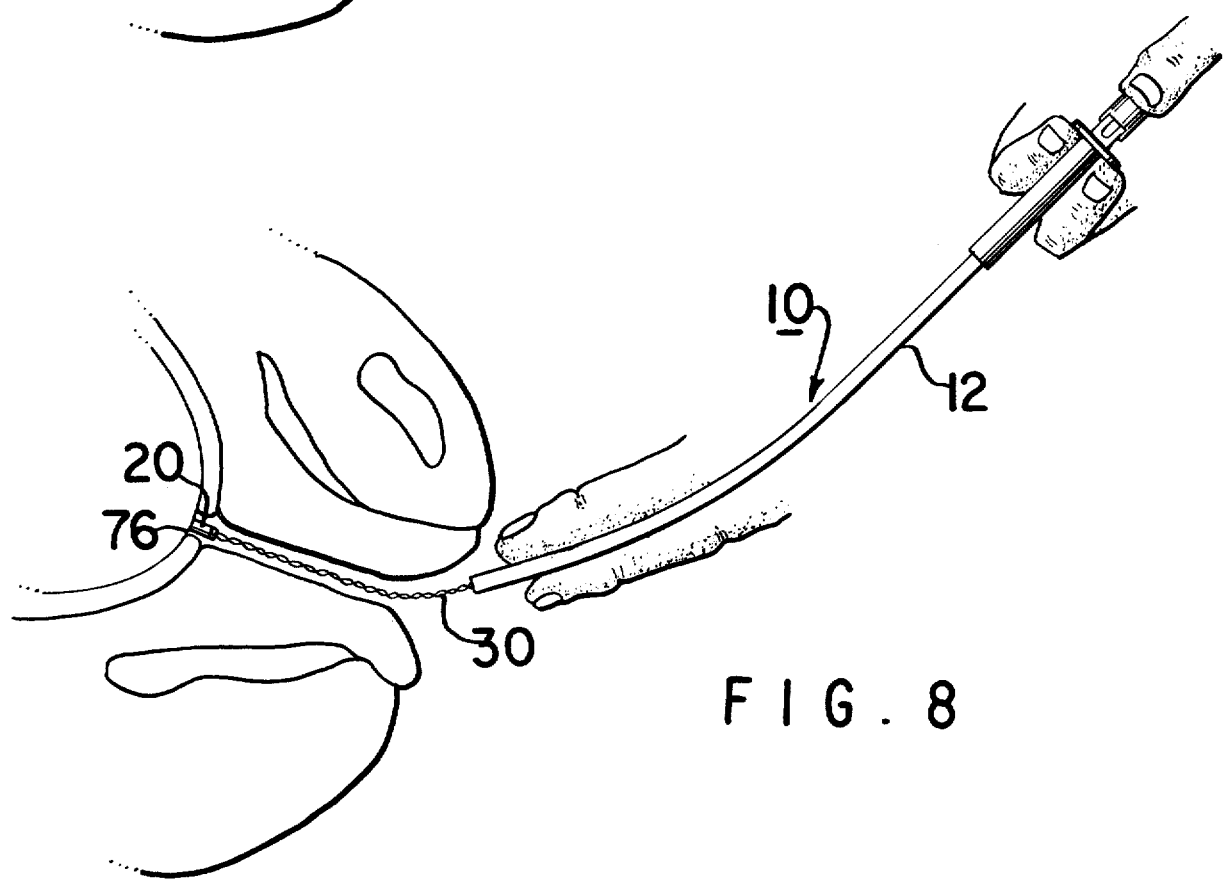

With reference to FIGS. 6, 7 and 8, a method of applying the signal acquisition means 20 using the electrode structure 10 is illustrated. With the signal acquisition means 20 disposed within the guide tube 12, the doctor inserts the forward end 14 of the guide tube 12 through the vagina 72 and cervix 74 until the forward end of the guide tube makes contact with the fetal presenting part 76, as shown in FIG. 6. The signal acquisition means 20 is maintained within the guide tube 12 by means of plug 68 which exerts a frictional retaining force against electrode wires 30. While maintaining the guide tube 12 thus positioned, the doctor places his thumb against cap 16 and his index and middle fingers against radial flange 52 of sleeve 50, as shown in FIG. 7, and draws the sleeve 50 back towards the cap 16, thus to advance the spiral retaining coil of the signal acquisition means 20 through the forward end 14 of the guide tube 12 and to rotate the drive member and the signal acquisition means 20 to screw the spiral retaining coil into the epidermis of the fetal presenting part 76. Since the advancement of the driving member automatically releases the electrode wires 30 from the frictional grip of plug 68, this step need not be performed by the busy doctor, as was necessary in the prior art. The use of an electrode structure in accordance with the present invention is further simplified by the provision of the axial extension 64 of cap 62, which acts as a stop limiting the rearward motion of the sleeve 50 so that the rotation of the spiral retaining coil is automatically limited to the desired $1\frac{1}{4}$ turns.

With reference to FIG. 8, the physician then withdraws the guide tube 12 from the vagina 72 without further adjusting his grip on the electrode structure 10. As the guide tube 12 is withdrawn, the signal acquisition means 20 remains in place on the fetal presenting part and the electrode wires are withdrawn through the driving member. The electrode wires are then coupled to an appropriate instrument to monitor the condition of the child as labor progresses.

It is intended that the present invention be limited only by the scope of the appended claims.

I claim:

1. An improved electrode structure for use in monitoring fetal heartbeat and the like, comprising:
    a guide tube having an open forward end adapted to be inserted through the vagina and cervix of a woman in labor;
    signal acquisition means adapted to rotatably engage a fetal epidermis; the signal acquisition means being rotatably disposed in the guide tube;
    a driving member rotatably disposed in the guide tube and positioned to engage the signal acquisition means to impart rotational motion thereto for driving the signal acquisition means into engagement with a fetal epidermis;
    a first line attached at a first end to the driving member and wrapped circumferentially around at least a portion of the driving member; and
    line unwinding means affixed to a second end of the line for pulling the line tangentially with respect to the driving member;
    whereby the driving member and the signal acquisition means may be rotated for engaging a fetal epidermis.

2. The electrode structure of claim 1, wherein the line unwinding means comprises means for withdrawing the first line through an aperture in the guide tube such that the driving member is thereby caused to rotate relative to the guide tube upon actuation of the line unwinding means.

3. The electrode structure of claim 2, wherein the means for withdrawing the first line comprises sliding means mounted externally to the guide tube and moveable axially with respect thereto for withdrawing the first line through the aperture.

4. The electrode structure of claim 3, wherein the sliding means comprises a sleeve having a radial flange adapted to be grasped by the user to apply a force thereto causing the sleeve to slide axially with respect to the guide tube.

5. The electrode structure of claim 1, wherein the signal acquisition means is slidably positioned adjacent the forward end of the guide tube and the driving member is slidably positioned rearwardly thereof for advancing the signal acquisition means through the forward end of the guide tube; and
further comprising retaining means for retaining the signal acquisition means within the guide tube while the first line remains fully wrapped on the driving member.

6. The electrode structure of claim 5, wherein the line unwinding means comprises means for withdrawing the first line through a first aperture in the guide tube such that the driving member is thereby caused to rotate relative to the guide tube upon actuation of the line unwinding means; and the retaining means comprises displacement means for displacing the first end of the first line rearwardly of the first aperture and means for maintaining the signal acquisition means against a forward end of the driving member.

7. The electrode structure of claim 6, wherein the displacement means comprises a second line attached at a first end to the driving member at a point spaced axially at a first distance from the first end of the first line, the second line passing through a second aperture in the guide tube and affixed at a second end to the line unwinding means, such that when the first line is fully wound on the drive member, the first end of the second line is aligned axially with the second aperture; and the first aperture is spaced axially from the second aperture by a second distance which is sufficiently smaller than the first distance such that when the first line is fully wound on the drive member, the latter is withdrawn sufficiently into the guide tube to permit retention of the signal acquisition means therein.

8. The electrode structure of claim 7, wherein the line unwinding means comprises a sliding means mounted externally to the guide tube and moveable axially with respect thereto, the second end of the second line being affixed thereto at a distance spaced axially from the second end of the first line, such that when the first line is unwound by an axial motion of the sliding means, the second line is caused to wind about the drive member, whereby an opposed axial motion of the sliding means will rewind the first line about the drive member.

9. The electrode structure of claim 5, wherein the signal acquisition means includes electrode wires extending rearwardly through the guide tube and the means for retaining comprises a plug having a forwardly projecting radial tab and secured in the guide tube rearwardly of the driving member, such that the driving member is frictionally engaged by an inner surface of the tab and the electrode wires are retained against forward displacement between a rear end of the driving member an a forward surface of the plug.

* * * * *